United States Patent [19]

Clayden

[11] Patent Number: 5,787,185
[45] Date of Patent: Jul. 28, 1998

[54] BIOMETRIC IDENTIFICATION OF INDIVIDUALS BY USE OF SUBCUTANEOUS VEIN PATTERNS

[75] Inventor: David Oswald Clayden, Isleworth, England

[73] Assignee: British Technology Group Ltd., London, England

[21] Appl. No.: 530,169

[22] PCT Filed: Mar. 31, 1994

[86] PCT No.: PCT/GB94/00707

§ 371 Date: Sep. 29, 1995

§ 102(e) Date: Sep. 29, 1995

[87] PCT Pub. No.: WO94/29747

PCT Pub. Date: Dec. 22, 1994

[30] Foreign Application Priority Data

Apr. 1, 1993 [GB] United Kingdom ............ 9306897

[51] Int. Cl.$^6$ ........................................ G06K 9/00
[52] U.S. Cl. ................................ 382/115; 382/275
[58] Field of Search ........................ 382/115, 124, 382/205, 274, 275, 260; 340/825.3, 825.31, 825.32, 825.33, 825.34, 825.35

[56] References Cited

U.S. PATENT DOCUMENTS

| | | | |
|---|---|---|---|
| 4,550,437 | 10/1985 | Kobayashi et al. | 382/205 |
| 4,571,635 | 2/1986 | Mahmoodi et al. | 382/274 |
| 4,699,149 | 10/1987 | Rice | 382/115 |
| 4,811,414 | 3/1989 | Fishbine et al. | 382/124 |
| 5,003,618 | 3/1991 | Meno | 382/274 |

FOREIGN PATENT DOCUMENTS 8804153  6/1988  WIPO.

*Primary Examiner*—Joseph Mancuso
*Attorney, Agent, or Firm*—Cushman Darby & Cushman IP Group of Pillsbury Madison & Sutro LLP

[57] ABSTRACT

A method of verifying the identity of an individual comprises capturing an image of the subcutaneous vein pattern at a predetermined region of the individual, converting the captured image to a plurality of stored values representative of the intensity of said image at specified relative locations, processing the stored values to produce a second plurality of stored values representative of the image of the vein pattern having enhanced contrast and subjecting the second plurality of stored values to a thresholding process to select those above a predetermined value and storing a set of measurements derived from the selected ones of said second plurality of stored values for comparison with a corresponding set of measurements made on the individual.

14 Claims, 5 Drawing Sheets

BIOMETRIC IDENTIFICATION OF INDIVIDUALS BY USE OF SUBCUTANEOUS VEIN PATTERNS

This application claims benefit of international application PCT/GB94/00707 filed Mar. 31, 1994.

BACKGROUND OF THE INVENTION

1. Field of the Invention

This invention relates to the biometric identification of individuals and, in particular, to methods and apparatus for detecting the locations of subcutaneous blood vessels and for encoding such locations for storage on identity cards. It finds particular application in the verification of identity in transactions involving such cards.

In this specification, the expression "vein pattern" is deemed to include the pattern of arteries, capillaries and other blood vessels.

2. Description of the Related Art

In British Patent No. 2156127 there is described a method and apparatus for the identification of individuals by means of subcutaneous patterns of blood vessels. One difficulty encountered with such apparatus is the poor signal-to-noise ratio when endeavouring to detect blood vessel locations, for example, in the back of the hand. This may be due to hairs, or the non-planar nature of the locations or uneven illumination.

SUMMARY OF THE INVENTION

We have now devised an improved method of verifying the identity of individuals. According to the present invention there is provided a method of verifying the identity of an individual comprising the steps of capturing an image of the subcutaneous vein pattern at a predetermined region of the individual, converting said captured image to a plurality of stored values representative of the intensity of said image at specified relative locations, processing said stored values to produce a second plurality of stored values representative of an image of said vein pattern having enhanced contrast and subjecting said second plurality of stored values to a thresholding process to select those above a predetermined value and storing a set of measurements derived from the selected ones of said second plurality of stored values for comparison with a corresponding set of measurements made on said individual.

BRIEF DESCRIPTION OF THE DRAWINGS

The invention will be particularly described with reference to the accompanying drawings, in which:-

DESCRIPTION OF THE PREFERRED EMBODIMENTS

Figure 1:
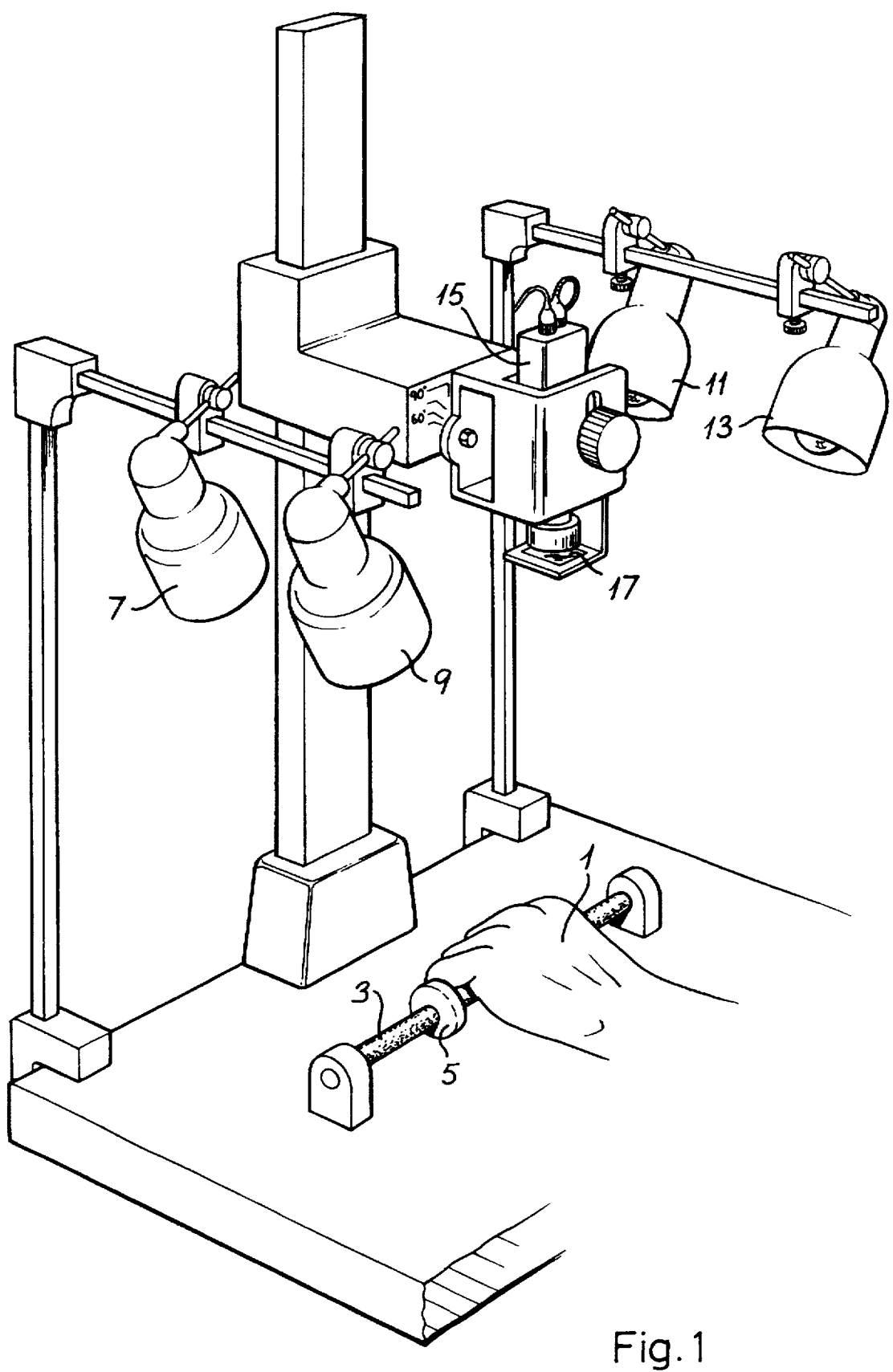
FIG. 1 is a perspective view of apparatus suitable for scanning vein patterns.

Referring now to the drawings, a hand 1 of an individual whose identity is to be verified is positioned approximately by gripping a positional reference handle 3. An optional side stop 5, against which the side of the hand abuts, provides an additional constraint. Even illumination is provided by four laterally-positioned incandescent lamps 7,9,11,13 which are under-run to provide an infra-red-rich emission spectrum. A video camera 15 is positioned directly above the hand position and produces a raster-scan image of the back of the hand. A band-pass filter 17 extracts an infra-red image and reduces the proportion of visible radiation. It therefore enhances the visibility of the subcutaneous vein pattern.

By viewing the vein pattern through a pair of filters having different transmission characteristics, it is possible to differentiate between veins and arteries, which have different relative contents of oxy-haemoglobin and carboxy-haemoglobin. This may be used as a basis for enhanced recognition tests or simply to verify that the hand is still attached and vital.

The two images may be obtained sequentially by substituting one filter for the other or simultaneously by means of a split image with one filter in each field of view.

Figure 2:
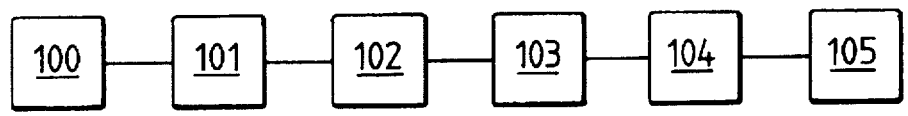
FIG. 2 is a block diagram of apparatus in accordance with a preferred embodiment of the invention.

Referring to FIG. 2, the output of the video camera 100 is transferred to a frame store 101. The raw Image from the video camera suffers from poor contrast and also from the effects of varying brightness across its width, due to the curved nature of the back of the hand.

Figure 3:
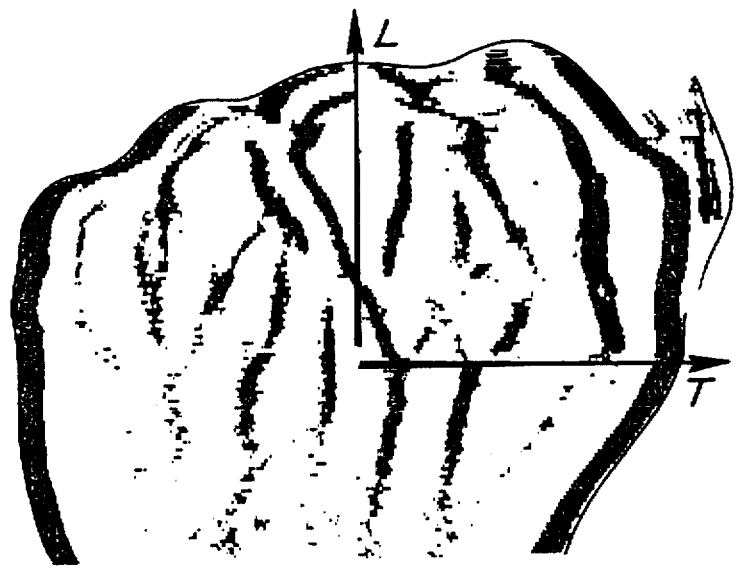
FIG. 3 shows a raw vein pattern obtained from the apparatus of FIG. 2.
Figure 4:
FIG. 4 shows the image of FIG. 3 after processing to enhance its contrast.

During a first signal processing step in signal processor 102, the amplitude of each pixel is weighted to enhance the local contrast. The contrast can be improved by employing a local contrast enhancement function, making use of the values at sampling points in the neighbourhood of each point in the plane. In general, the design of a local contrast enhancement function is a compromise between performance and speed. The particular function chosen in the preferred embodiment is a single-dimensional one employing six points in a line transverse to the axis of the hand. The amplitude at a particular point is derived from the sum of the amplitudes of the two immediately-adjacent pixels and the pixels at a distance of ±10 and ±20 pixels therefrom. The immediate neighbouring pixels are given a weighting factor of +2 and the amplitudes of the pixels at ±10 and ±20 pixels spacing are given a weighting factor of −1. The sum of these six weighted values is then taken to give a net value for each position. The effect of this weighting regime is to produce a blood vessel pattern with an enhancement of the longitudinal (in the direction L) blood vessels at the expense of the transverse ones (in the direction T). This image is subjected to a thresholding process in a threshold detector 103 to produce a black and white pattern. (FIG. 3) The black and white image is also preferably subjected to an area thresholding process to remove small white artifacts in the black regions and small black objects in the white regions. (FIG. 4)

We have found that, in practice, there is sufficient information content in the longitudinal blood vessels to permit adequate identification to be performed and that the attenuated image of the transverse blood vessels is not disadvantageous. On the other hand, this step reduces the demands placed on the data handling and storage requirements of the system.

The cleaned-up black and white image of the blood vessel is then converted in a further signal processor 104 to a series of vectors, which are a series of small straight lines approximating to the center line of each blood vessel. These vectors may be used for various purposes (a) to measure misalignment of one image relative to another, both rotationally and longitudinal and lateral displacement (b) to obtain a score for the probability that the two compared images are of the same blood vessel pattern and (c) to provide compressed data description of a vein pattern which can be used as a reference template. They are stored in an output device 105.

The transverse resolution of the video camera is five hundred and twelve pixels, of which about two thirds occur in the width of the hand—there is a gap at either side—equivalent to about four hundred pixels across the hand. Longitudinally, it is 128 lines. The width of a vein is typically about two millimetres.

An objective of the signal processing is to improve the signal-to-noise ratio so that spurious results will not, for example be caused by hairs on the back of the hand.

Signal-to-noise ratio is enhanced by the weighting regime adopted.

Figure 5:
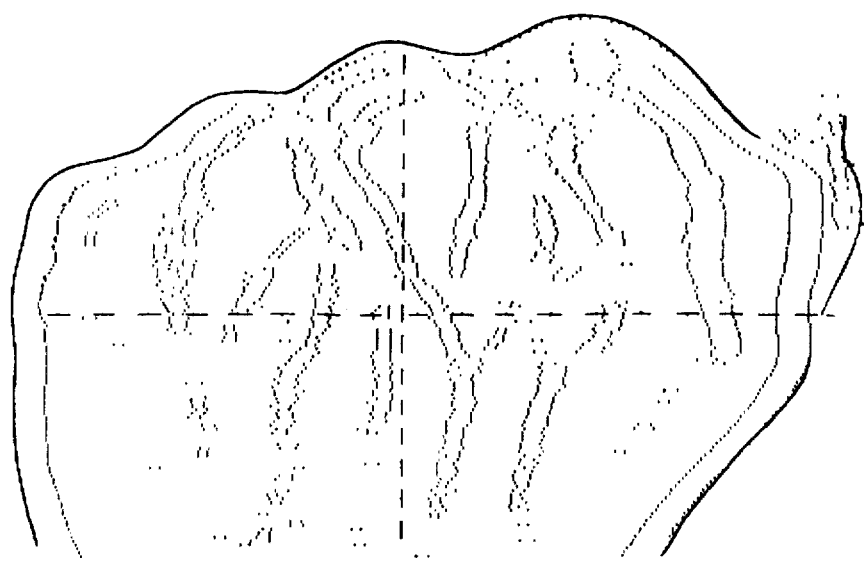
FIG. 5 shows the image of FIG. 4 after processing to reveal boundary lines.
Figure 6:
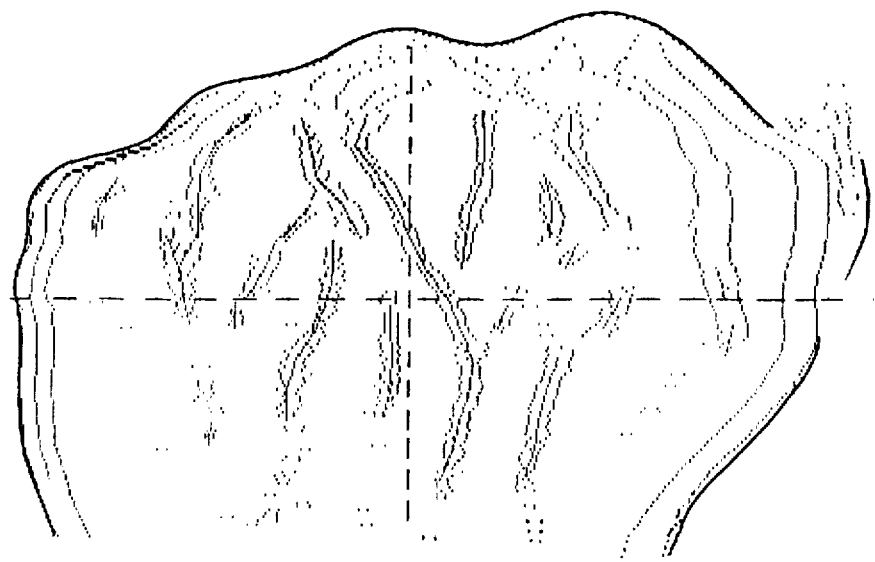
FIG. 6 shows a pattern of vectors imposed on the image of FIG. 5.
Figure 7:
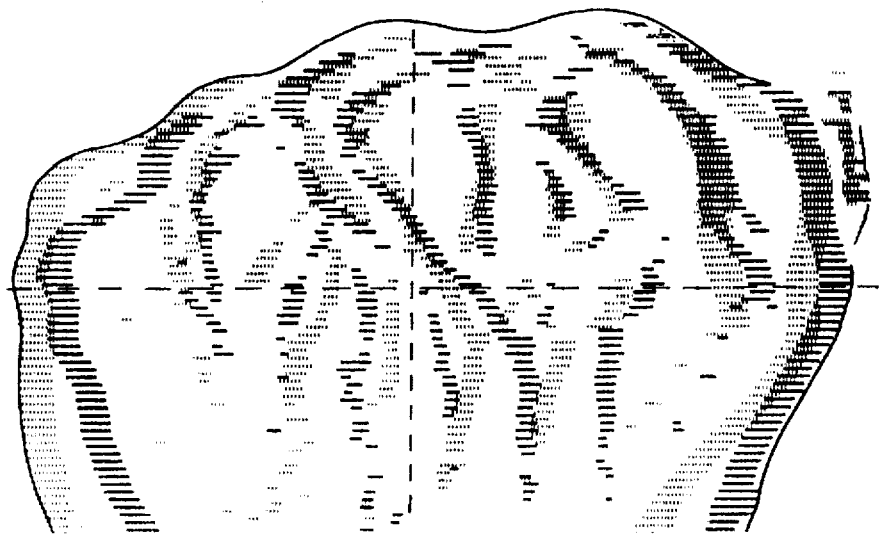
FIG. 7 shows two superimposed vein patterns.
Figure 8:
FIG. 8 shows the vein patterns after alignment.

FIG. 5 shows the image of FIG. 4 after processing to reveal the boundary lines and FIG. 6 shows a pattern of vectors imposed on the image of FIG. 5. FIG. 7 shows a first vein image (lightly dotted lines) superimposed on a second vein image (heavy dotted lines) and FIG. 8 shows the images after alignment.

A variety of methods may be used for measuring the similarity of two vein patterns.

Figure 9:
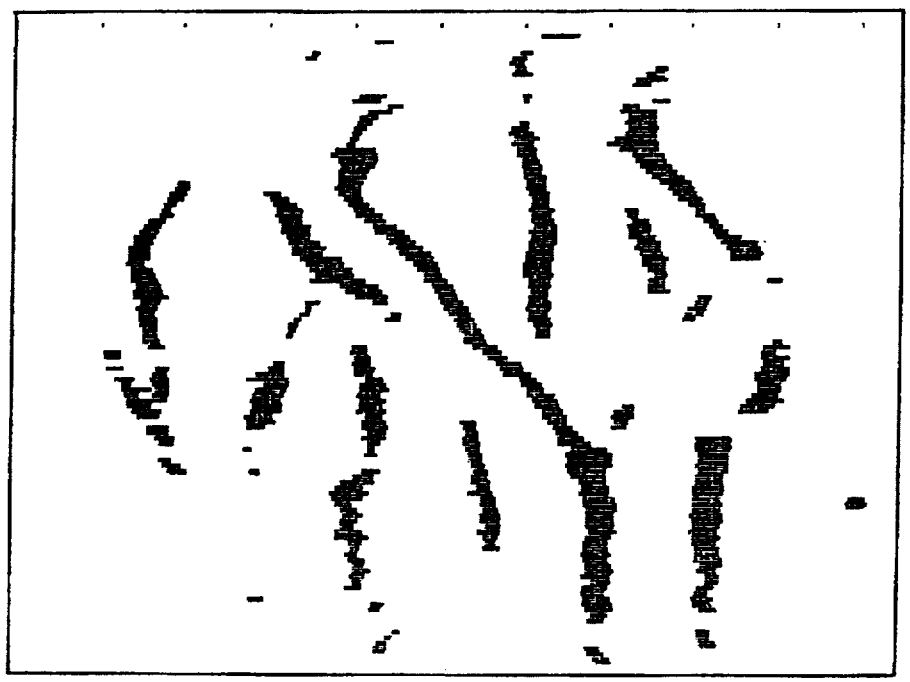
FIG. 9 shows the matched portions of the two superimposed patterns.
Figure 10:
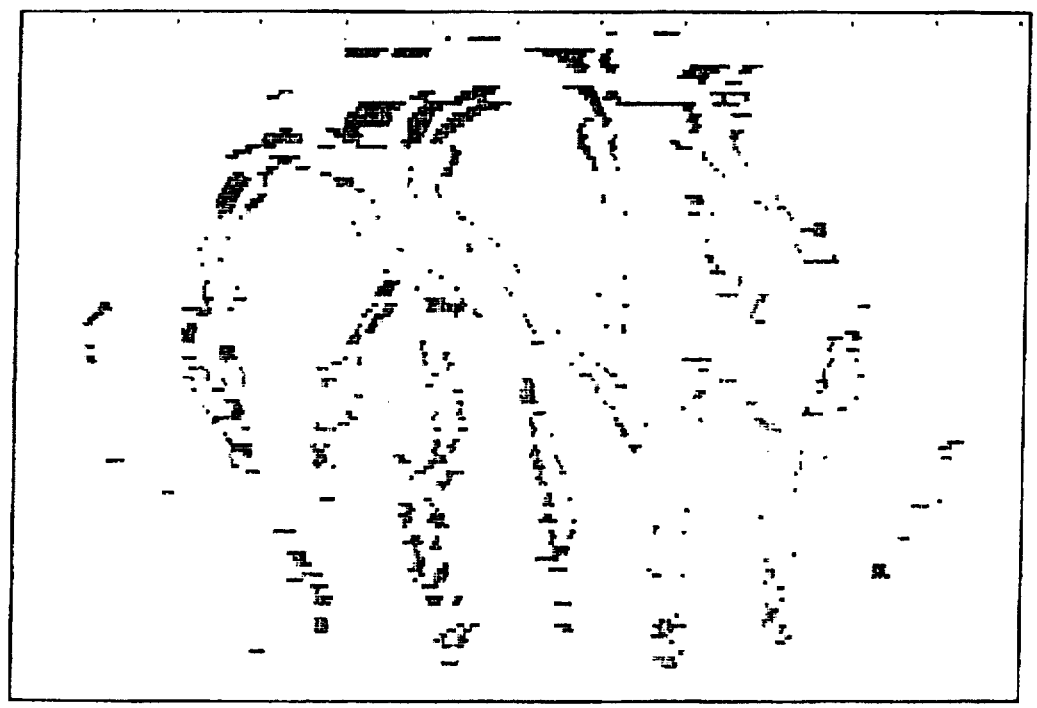
FIG. 10 shows the mismatched portions of the vein patterns.

A first image is captured to a first plurality of stored values which represent an intensity of the image at specified relative locations. A second plurality of stored values is determined, in the preferred embodiment, by employing six points in a line traverse to the axis of the hand. A first pair of amplitudes is measured at pixels on either side of a given point and a second pair of amplitudes at ten pixels on either side of the given point. A third pair of amplitudes is measured at twenty pixels on either side of the given point. The first pair of amplitudes is given a weighting of 2 and the second and the third set of amplitudes are given a weighting of −1. The sum of these six weighted values is then taken to give a net value for each position. As mentioned previously, the effect of the weighting is to produce a blood vessel pattern, enhancing the longitudinal blood vessels at the expense of the traverse ones. Further processing may be performed to remove small area artifacts in the vein patterns. (FIG. 9) this is divided by the area of the non-coinciding part of the patterns (Logical XOR) (FIG. 9) Typical results for a pair of well aligned pair of patterns taken from the same hand at different times is 1.5, whilst the best an imposter can achieve is about 0.25.

A second variation involves measuring the total length of vein center-line which falls within a pre-determined tolerance of the center-line of the other image.

By using a compressed template and a test pattern, after alignment a score can be calculated by counting the number of vector ends (or vector centers) which fall within (or close to) the outline of the test pattern. The ratio of these two values will give a score similar to that of method 1.

Variation 4 involves using a compressed template and the center-lines of a test pattern. The test is set by the length of center-line which falls within a predetermined tolerance of the vectors of the template after alignment.

A fifth method uses two sets of vectors, a test pattern and a corresponding pattern derived from measurements on an individual, and accesses the misalignment of the vector ends of one pattern and the vectors of the other pattern.

I claim:

1. A method of verifying an identity of an individual comprising steps of:

capturing a first image of a subcutaneous vein pattern at a predetermined region of the individual;

converting the captured first image to a plurality of first stored values representative of an intensity of the first image at specified relative locations, processing the first stored values to produce a second plurality of directionally-weighted stored values representative of a second image of [said] the vein pattern having enhanced contrast;

subjecting the second plurality of directionally-weighted stored values to a thresholding process to select ones of the second plurality of directionallyweighted stored values being above a predetermined value; and storing a set of measurements derived from selected ones of the second plurality of directionally-weighted stored values for comparison with a corresponding set of measurements made on the individual.

2. The method according to claim 1, wherein:

the step of processing comprises.

determining a mean of measurements taken at a given point and predetermined points on opposite sides of the given point weighted to give greater effect to a measurement taken at the given point.

3. The method according to claim 2, wherein:

a value in the second plurality of directionally-weighted stored values is determined by measuring a first pair of amplitudes at pixels on either side of the given point, a second pair of amplitudes at ten pixels on either side of the given point and a third pair of amplitudes at twenty pixels on either side of the given point and the first pair of amplitudes is given a weighting of 2 and the second and the third pair of amplitudes is given a weighting of −1.

4. The method according to any one of the preceding claims further comprising processing the second plurality of directionally-weighted stored values to remove ones of the second plurality of directionally-weighted stored values corresponding to small area artifacts in the vein pattern.

5. The method according to claim 1 further comprising:

comparing the set of measurements derived from the selected ones of the second plurality of directionally-weighted stored values with the corresponding set of measurements made on the individual, comprising:

measuring an area of patterns which coincide and dividing the measurements by an area of a non-coinciding part of the patterns to produce a ratio.

6. The method according to claim 51 wherein an acceptance/rejection threshold is the ratio of 1.

7. The method according to claim 6, wherein a rejection threshold is a ratio of 0.25.

8. The method according to claim 5, wherein a rejection threshold is a ratio of 0.25.

9. The method according to claim 5, wherein an acceptance threshold is the ratio of 1.5.

10. The method according to claim 1, further comprising:

comparing the set of measurements derived from the selected ones of the second Plurality of directionally-weighted stored values with the corresponding set of measurements made on the individual, comprising:

measuring a total length of vein center-line which falls within a pre-determined tolerance of a center-line of another image.

11. The method according to claim 1, further comprising:

comparing the set of measurements derived from the selected ones of the second plurality of directionally-weighted stored values with the corresponding set of measurements made on the individual, comprising:

using a compressed template and a test pattern, after alignments to calculate a score by counting an amount of a predetermined part of a vector which falls within an outline of the test pattern.

12. The method according to claim 1, further comprising:

comparing the set of measurements derived from the selected ones of the second plurality of directionally-weighted stored values with the corresponding set of measurements made on the individual, comprising:

using a compressed template and a test pattern, after alignment to calculate a score by measuring a length of a center-line which falls within a predetermined tolerance of vectors of the compressed template.

13. The method according to claim 1, further comprising:

comparing the set of measurements derived from the selected ones of the second plurality of directionally-weighted stored values with the corresponding set of measurements made on the individual, comprising:

using two sets of vectors having vector ends and assessing a misalignment of the vector ends of one pattern and the vectors of another pattern.

14. An apparatus for verification of an identity of an individual comprising:

means for capturing an image of a subcutaneous pattern of veins at a predetermined region of the individual and deriving signals corresponding to the image;

means for enhancing a contrast of the signals by producing a plurality of directionally-weighted stored values; and detector means for detecting ones of the plurality of directionally-weighted stored values in excess of a predetermined threshold.

* * * * *